US00PP28620P3

(12) United States Plant Patent
Dobres et al.

(10) Patent No.: US PP28,620 P3
(45) Date of Patent: Nov. 7, 2017

(54) ***SALVIA* PLANT NAMED 'NOVASALRED'**

(50) Latin Name: *Salvia hybrida*
Varietal Denomination: Novasalred

(71) Applicant: CP DELAWARE, INC., Wilmington, DE (US)

(72) Inventors: Michael S. Dobres, San Javier (ES); Jessica D. Janes, Elkton, MD (US)

( * ) Notice: Subject to any disclaimer, the term of this patent is extended or adjusted under 35 U.S.C. 154(b) by 15 days.

(21) Appl. No.: 14/757,360

(22) Filed: Dec. 22, 2015

(65) Prior Publication Data

US 2017/0181356 P1 Jun. 22, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct *Salvia* plant was formed by controlled breeding followed by selection. Over a long blooming season attractive red blossoms are formed. The growth habit is compact and bushy. The blossoms are borne on sturdy stems. The plant can be readily asexually reproduced by the rooting of cuttings. Hardiness is displayed to at least U.S.D.A. Hardiness Zone No. 7. The plant is well suited for providing attractive colorful ornamentation in parks, gardens, public areas, and residential landscapes.

2 Drawing Sheets

Botanical/commercial classification: *Salvia hybrida/Salvia* Plant.

Varietal denomination: cv. Novasalred.

SUMMARY OF THE INVENTION

The new cultivar of *Salvia hybrida* was created by artificial pollination carried out at West Grove, Pa., U.S.A., during January 2011 wherein two parents were crossed which previously had been studied in the hope that they would contribute desired characteristics. The name designations of the female parent (i.e., seed parent) and male parent (i.e., pollen parent) are unknown.

The seeds resulting from the pollination were collected during 2011, were grown in tissue culture, the resulting young plants were acclimated to greenhouse growing conditions in the fall of 2011, and were thereafter studied for the possible presence of novel attractive phenotypes. The resulting plants were physically and biologically different from each other. Selective study resulted in the identification of a single plant of the new cultivar. A plant of the present invention was selected during the summer of 2012 primarily in view of its abundance of attractive long-lasting true red flowers, vigorous green foliage, and sturdy stems. Had this new plant not been selected and preserved, it would have been lost to mankind.

The plant is a perennial that can be grown to advantage without protection in U.S.D.A. Hardiness Zone No. 7. Also, established plants have appeared to exhibit adaptability to U.S.D.A. Hardiness Zone No. 6.

It was found that the new *Salvia* cultivar possesses the following combination of characteristics:

(a) displays a compact and bushy growth habit with sturdy stems, (b) forms in abundance over extended blooming season attractive red blossoms, (c) displays hardiness to at least U.S.D.A. Hardiness Zone No. 7, (d) displays vigorous green foliage, and (e) is well suited for providing attractive ornamentation.

The new cultivar of the present invention can be readily distinguished from other *Salvia* cultivars such as the 'San Carlos Festival' cultivar (non-patented), the 'Ultra Violet' cultivar (U.S. Plant Pat. No. 21,411), the 'Bright Eyes' cultivar (U.S. Plant Pat. No. 22,491), the Orchid Glow cultivar (U.S. Plant Pat. No. 22,520), and the 'Golden Girl' cultivar (U.S. Plant Pat. No. 23,997) through an inspection of the blossoms. More specifically, the 'San Carlos Festival' cultivar displays magenta blossoms, the 'Bright Eyes' cultivar displays red blossoms with a readily apparent white eye at the center and less sturdy branches, and the 'Orchid Glow' cultivar and 'Ultra Violet' cultivar display purple blossoms.

The new cultivar well meets the needs of the horticultural industry and can be grown to advantage as attractive colorful ornamentation in parks, gardens, public areas, and residential landscapes.

The new cultivar has been asexually reproduced by the rooting of cuttings for several generations. Such asexual reproduction as performed at West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Novasalred', and will be marketed under the RED ARTIC BLAZE Trademark.

BRIEF DESCRIPTION OF THE PHOTOGRAPHS

The accompanying photographs show the new cultivar as nearly true as it is reasonably possible to make the same, in color illustrations of this character. The photographs were obtained during October 2013 at West Grove, Pa., U.S.A., and illustrate typical one-year-old plants while being grown outdoors.

DETAILED BOTANICAL DESCRIPTION

Figure 1:
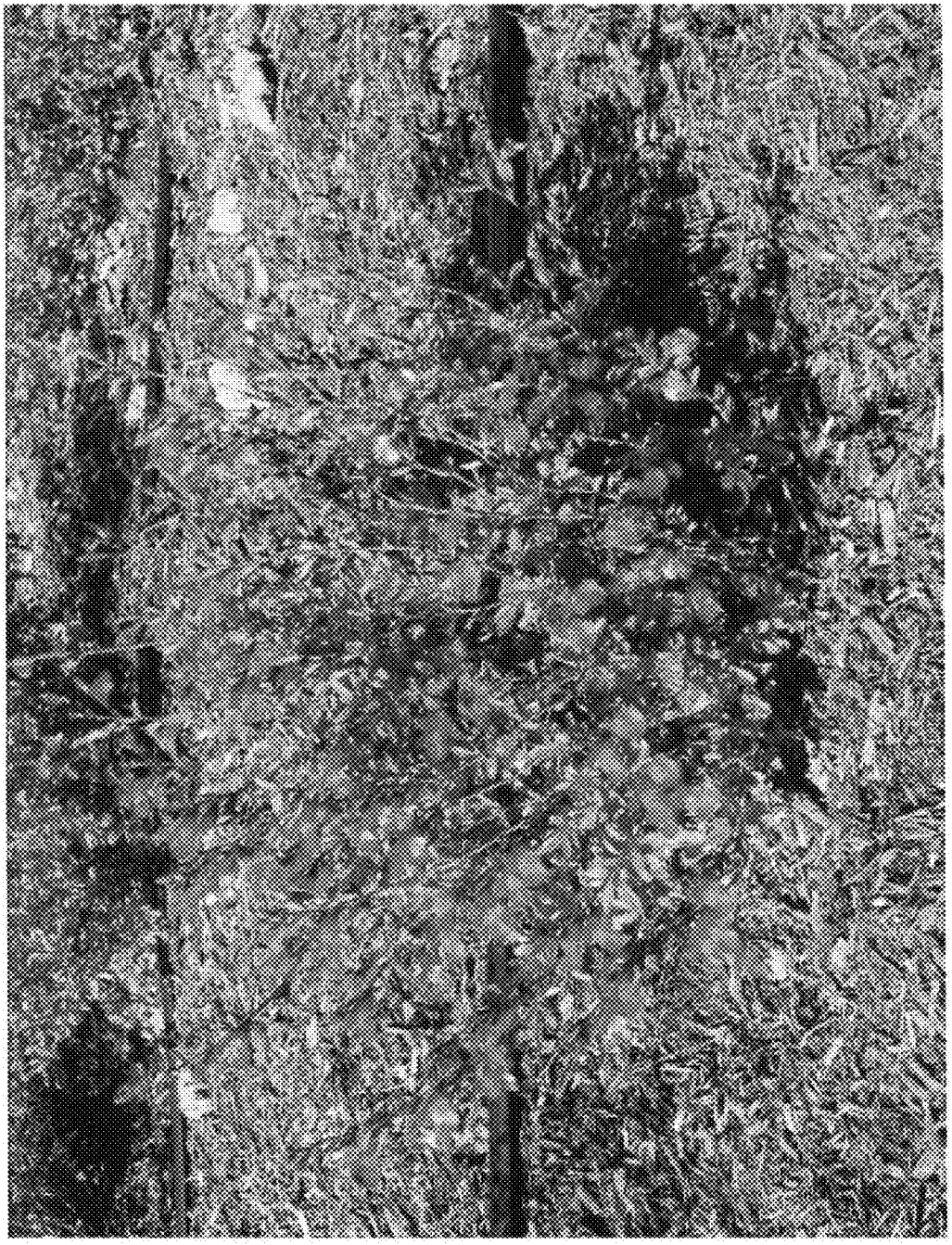
FIG. 1 illustrates the overall compact and bushy growth habit of a flowering plant of the new cultivar while being grown in the ground.
Figure 2:
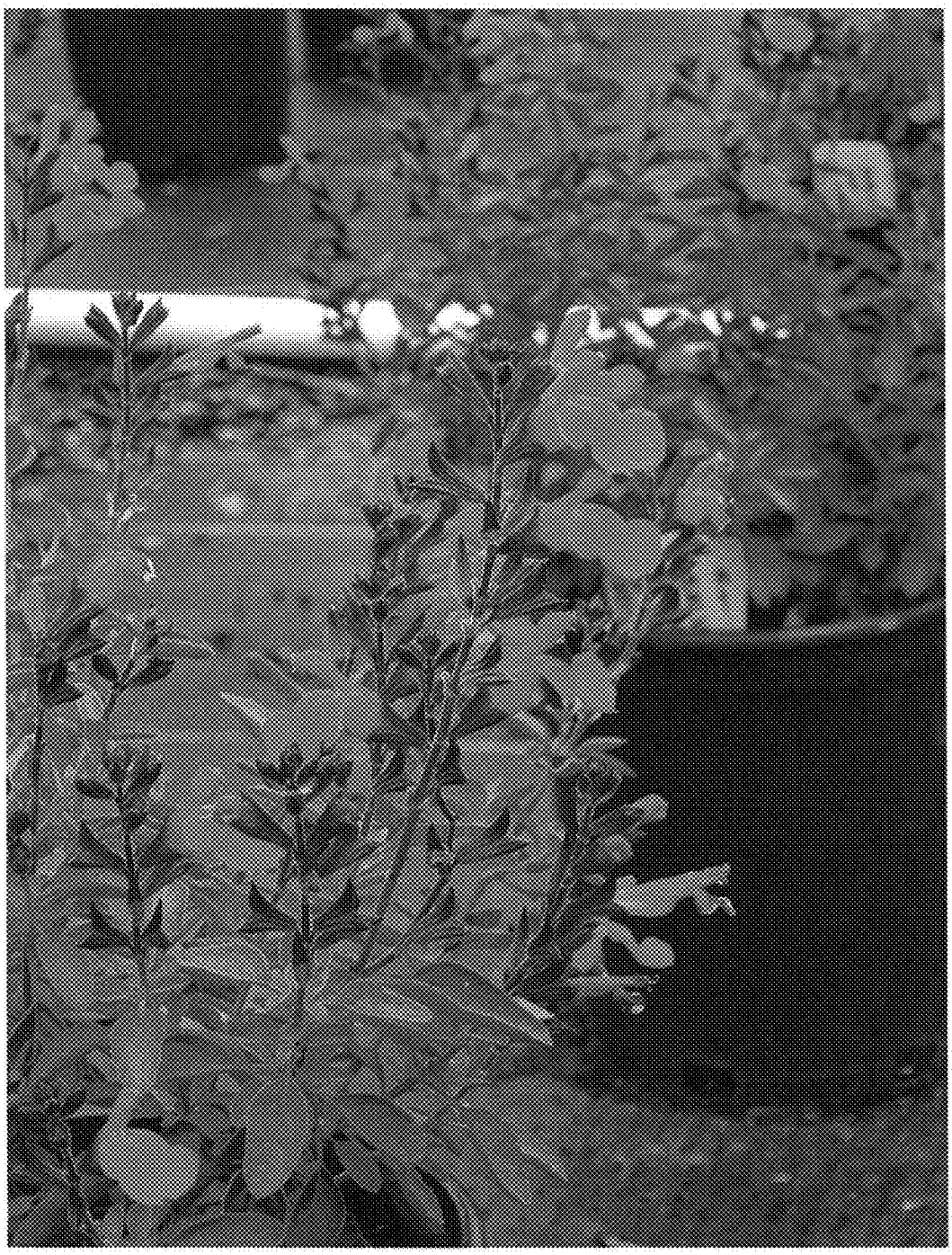
FIG. 2 illustrates a closer view of the attractive red blossoms and foliage of the new cultivar while being grown in a container.

The chart used in the identification of colors is that of The Royal Horticultural Society (R.H.S. Colour Chart) of London, England (1995). The description is based on the observation of typical specimens of the new cultivar at an age of approximately one year during August 2015 while growing indoors in containers at West Grove, Pa., U.S.A.

Plant:

*Form*.—Compact and bushy, and generally fuller than that of the 'Bright Eyes' cultivar.

*Height*.—Commonly up to approximately 40 cm on average.

*Width*.—Commonly approximately 45 cm on average.

*Growth habit*.—Perennial in U.S.D.A. Hardiness Zone Nos. 7 to 11, with established plants exhibiting adaptability to U.S.D.A. Hardiness Zone No. 6 during observations to date.

*Lateral branch number*.—17 on average per two-year-old plant growing indoors in container.

*Lateral branch color*.—Commonly near Brown Group N200B.

*Lateral branch texture*.—Commonly scabrous with older wood being more rugulose.

*Lateral branch length*.—Approximately 48 cm on average.

*Lateral branch diameter*.—Approximately 0.6 cm on average.

*Lateral branch internode length*.—Approximately 1.75-2.5 cm on average.

*Leaf arrangement*.—Opposite.

*Leaf configuration*.—Elliptic to oblong.

*Leaf length*.—Commonly approximately 4 cm on average.

*Leaf width*.—Commonly approximately 1.5 cm on average.

*Leaf margin*.—Entire.

*Leaf venation*.—Pinnipalmate pattern, and color is commonly near Green Group 143B.

*Leaf texture*.—Commonly slightly fleshy.

*Leaf blade color*.—Near Green Group 137B on the upper surface, and near Green Group 137C on the under surface.

*Leaf blade apex*.—Acute to obtusely rounded.

*Leaf blade base*.—Mainly obtuse.

*Scent*.—Leaves commonly display a tangy fruity scent when crushed.

*Petiole shape*.—Somewhat flattened.

*Petiole length*.—Variable and commonly approximately 1 cm on average.

*Petiole width*.—Commonly approximately 1 mm.

*Petiole color*.—Near Green Group 143C.

Inflorescence:

*Type*.—Terminal raceme.

*Diameter*.—Commonly approximately 4 cm on average.

*Length*.—Commonly approximately 28 cm on average. number commonly up to approximately 100 flowers per plant on average are in bloom at a given time.

*Configuration*.—Tubular, and two-lipped.

*Flower bud shape*.—Typically teardrop.

*Flower bud color*.—Commonly near Red-Purple Group 58B.

*Flower bud length*.—Approximately 1.25 cm on average.

*Flower bud diameter*.—Approximately 0.5 cm on average.

*Pedicel length*.—Commonly approximately 5 mm on average.

*Pedicel width*.—Commonly less than 1 mm.

*Pedicel color*.—Near Green Group 143C and overlaid with Red-Purple Group 59A.

*Pedicel pubescence*.—Present, with the pedicel being puberulent.

*Calyx shape*.—Broadly cam panulate and flared towards the apex.

*Calyx rib number*.—Commonly 13 on average and longitudinally disposed.

*Calyx length*.—Commonly approximately 1.5 cm on average.

*Calyx width*.—Commonly up to approximately 1.2 cm.

*Calyx texture*.—Puberulent on the upper and under surfaces.

*Calyx color*.—On the upper lobe near Green Group 143A overlaid with Red-Purple Group 59A towards the apex, and on the lower lobes near Green Group 143C overlaid with Red-Purple Group 59A towards the apex.

*Calyx lobe number*.—3.

*Calyx upper lobe number*.—1.

*Calyx upper lobe shape*.—Acute.

*Calyx upper lobe length*.—Commonly approximately 1.2 cm on average.

*Calyx upper lobe width*.—Commonly approximately 6 mm in width on average.

*Calyx lower lobe number*.—2.

*Calyx lower lobe shape*.—Acute.

*Calyx lower lobe length*.—Commonly approximately 1.1 cm on average.

*Calyx lower lobe width*.—Commonly approximately 7 mm on average.

*Corolla shape*.—Tubular proximally to two-lipped distally.

*Corolla length*.—Commonly approximately 2.5 cm on average.

*Corolla color*.—The base commonly is near White Group 155C, the tube is near Red Group 51A, and the lower lip is near Red Group 50A. The white coloration at the base is visible upon dissection only.

*Corolla tube length*.—Approximately 1.5 cm on average.

*Corolla tube depth*.—Approximately 6 mm on average.

*Corolla tube lip number*.—1.

*Corolla upper lip number*.—2.

*Corolla upper lip shape*.—Hood-like.

*Corolla upper lip length*.—Commonly approximately 9 mm average.

*Corolla lower lip length*.—2, suborbicular.

*Corolla lower lip shape*.—Banner-like, and extended downward.

*Corolla lower lip outline*.—Obovate.

*Corolla lower lip length*.—Commonly approximately 1.2 cm on average.

*Corolla lower lip diameter at tip*.—Approximately 1.2 cm on average.

*Style length*.—Approximately 2.1 cm on average.

*Style width*.—Commonly less than 1 mm.

*Style attachment site*.—At four-lobed ovary between lobes.

*Ovary*.—Approximately 2 mm in length, approximately 2 mm in diameter, and near Yellow-Green Group 145A in coloration.

*Stamen number*.—1.

*Stamen shape*.—Seesaw-like.

*Filament length*.—Approximately 1.2 cm on average.

*Connective length*.—Approximately 5 mm on average.

*Anther length*.—Approximately 2 mm on average.

*Anther diameter*.—Less than 1 mm.

*Anther color*.—Near Yellow-Orange Group 18A.

*Anther attachment site*.—At outer end of the connective.

*Pollen*.—Moderately formed.

*Fertility*.—Good.

*Seed*.—Commonly oval in shape, and commonly 1-4 seeds per pod on average.

Development:

*Vegetation*.—Well-branched with sturdy stems.

*Blooming*.—Displays a strong propensity to reblossom from spring through fall.

*Number of days to initiate roots*.—Approximately 10-14 days on average.

*Number of days to produce a rooted cutting*.—Approximately 28-35 days on average.

*Winter hardiness*.—The plant is a perennial that can be grown in U.S.D.A. Hardiness Zone Nos. 7 to 11, with established plants exhibiting adaptability in U.S.D.A. Hardiness Zone No. 6.

*Disease resistance*.—Typical for *Salvia* with no particular sensitivity to disease having been encountered during observations to date. The new 'Novasalred' cultivar has not been observed under all possible environmental conditions. Accordingly, it is possible that the phenotypic expression may vary somewhat with changes in light intensity and duration, cultural practices, and other environmental conditions.

We claim:

1. A new and distinct *Salvia* plant characterized by the following combination of characteristics:

(a) displays a compact and bushy growth habit with sturdy stems, (b) forms in abundance over an extended blooming season attractive red blossoms, (c) displays hardiness to at least U.S.D.A. Hardiness Zone No. 7, (d) displays vigorous green foliage, and (e) is well suited for providing attractive ornamentation; substantially as illustrated and described.

* * * * *